(12) United States Patent
Kapur et al.

(10) Patent No.: US 9,393,384 B1
(45) Date of Patent: Jul. 19, 2016

(54) SYSTEMS AND METHODS FOR TREATING ACUTE AND CHRONIC HEART FAILURE

(71) Applicant: Tufts Medical Center, Inc., Boston, MA (US)

(72) Inventors: Navin K. Kapur, Hanover, MA (US); Richard H. Karas, Franklin, MA (US)

(73) Assignee: Tufts Medical Center, Inc., Boston, MA (US)

( * ) Notice: Subject to any disclaimer, the term of this patent is extended or adjusted under 35 U.S.C. 154(b) by 0 days.

(21) Appl. No.: 14/828,429

(22) Filed: Aug. 17, 2015

(51) Int. Cl.
*A61M 29/00* (2006.01)
*A61M 25/10* (2013.01)

(52) U.S. Cl.
CPC . *A61M 25/10184* (2013.11); *A61M 2025/1052* (2013.01); *A61M 2205/3331* (2013.01); *A61M 2230/005* (2013.01); *A61M 2230/30* (2013.01)

(58) Field of Classification Search
CPC .............. A61M 2025/1052; A61M 25/1018; A61M 25/10184; A61M 5/1723; A61M 5/16831
USPC ............. 604/99.01, 509, 503, 96.01; 606/194
See application file for complete search history.

(56) References Cited

U.S. PATENT DOCUMENTS

| 4,546,759 A | 10/1985 | Solar | |
|---|---|---|---|
| 8,876,850 B1 * | 11/2014 | Vollmers | A61M 25/1018 604/288.01 |
| 2006/0064059 A1 * | 3/2006 | Gelfand | A61B 5/02028 604/103.06 |
| 2010/0331876 A1 | 12/2010 | Cedeno | |

* cited by examiner

*Primary Examiner* — Kevin C Sirmons
*Assistant Examiner* — Deanna K Hall
(74) *Attorney, Agent, or Firm* — Christopher C. Bolten; Nicola A. Pisano; Foley & Lardner LLP

(57) ABSTRACT

Systems and methods and devices are provided for arresting or reversing the effects of myocardial remodeling and degeneration after cardiac injury, without the potential drawbacks associated with previously existing systems and methods, by at least partially occluding flow through the superior vena cava over multiple cardiac cycles, and more preferably, by adjusting the interval or degree of occlusion responsive to a sensed level of patient activity. In some embodiments, a controller is provided that actuates a drive mechanism responsive to a sensed level of patient activity to provide at least partial occlusion of the patient's superior vena cava, while a data transfer circuit of the controller provides bi-directional transfer of physiologic data to the patient's smartphone or tablet to permit display and review of such data.

12 Claims, 12 Drawing Sheets

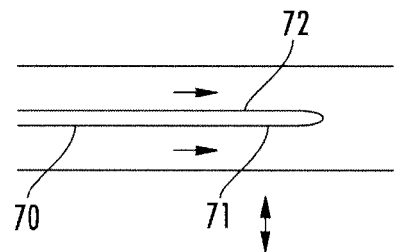
FIG. 8A
FIG. 8B
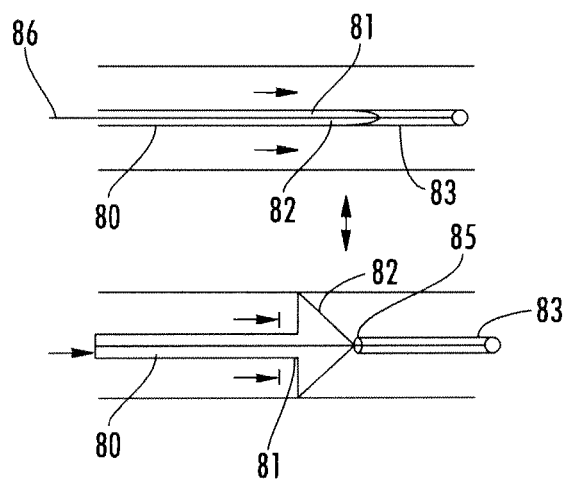
FIG. 9A
FIG. 9B
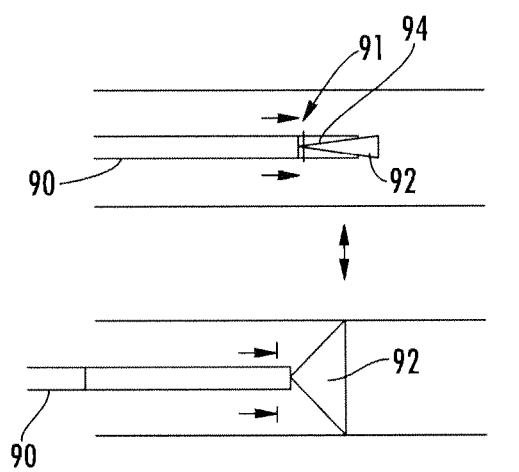
FIG. 10A
FIG. 10B ☐ Partial IVC Occlusion vs ■ Full SVC Occlusion  (2.5 Hours, n=1)

SYSTEMS AND METHODS FOR TREATING ACUTE AND CHRONIC HEART FAILURE

I. FIELD OF THE INVENTION

The disclosure relates to methods and systems for improving cardiac function in patients suffering from heart failure including patients with reduced ejection fraction.

II. BACKGROUND OF THE INVENTION

Heart failure is a major cause of global mortality. Heart failure often results in multiple long-term hospital admissions, especially in the later phases of the disease. Absent heart transplantation, the long term prognosis for such patients is bleak, and pharmaceutical approaches are palliative only. Consequently, there are few effective treatments to slow or reverse the progression of this disease.

Heart failure can result from any of multiple initiating events. Heart failure may occur as a consequence of ischemic heart disease, hypertension, valvular heart disease, infection, inherited cardiomyopathy, pulmonary hypertension, or under conditions of metabolic stress including pregnancy. Heart failure also may occur without a clear cause—also known as idiopathic cardiomyopathy. The term heart failure encompasses left ventricular, right ventricular, or biventricular failure.

While the heart can often initially respond successfully to the increased workload that results from high blood pressure or loss of contractile tissue, over time this stress induces compensatory cardiomyocyte hypertrophy and remodeling of the ventricular wall. In particular, over the next several months after the initial cardiac injury, the damaged portion of the heart typically will begin to remodel as the heart struggles to continue to pump blood with reduced muscle mass or less contractility. This in turn often leads to overworking of the myocardium, such that the cardiac muscle in the compromised region becomes progressively thinner, enlarged and further overloaded. Simultaneously, the ejection fraction of the damaged ventricle drops, leading to lower cardiac output and higher average pressures and volumes in the chamber throughout the cardiac cycle, the hallmarks of heart failure. Not surprisingly, once a patient's heart enters this progressively self-perpetuating downward spiral, the patient's quality of life is severely affected and the risk of morbidity skyrockets. Depending upon a number of factors, including the patient's prior physical condition, age, sex and lifestyle, the patient may experience one or several hospital admissions, at considerable cost to the patient and social healthcare systems, until the patient dies either of cardiac arrest or any of a number of co-morbidities including stroke, kidney failure, liver failure, or pulmonary hypertension.

Currently, there are no device-based solutions that specifically target a reduction in preload to limit the progression of heart failure. Pharmaceutical approaches are available as palliatives to reduce the symptoms of heart failure, but there exists no pharmaceutical path to arresting or reversing heart failure. Moreover, the existing pharmaceutical approaches are systemic in nature and do not address the localized effects of remodeling on the cardiac structure. It therefore would be desirable to provide systems and methods for treating heart failure that can arrest, and more preferably, reverse cardiac remodeling that result in the cascade of effects associated with this disease.

Applicants note that the prior art includes several attempts to address heart failure. Prior to applicants' invention as described herein, there are no effective commercial devices available to treat this disease. Described below are several known examples of previously known systems and methods for treating various aspects of heart failure, but none appear either intended to, or capable of, reducing left ventricular end diastolic volume ("LVEDV"), left ventricular end diastolic pressure ("LVEDP"), right ventricular end diastolic volume ("R down VEDV"), or right ventricular end diastolic pressure ("RVEDP") without causing possibly severe side-effects.

For example, U.S. Pat. No. 4,546,759 to Solar describes a triple balloon catheter designed for placement such that a distal balloon intermittently occludes the superior vena cava, a proximal balloon intermittently occludes the inferior vena cava, and an intermediate balloon expands synchronously with occurrence of systole of the right ventricle, thereby enhancing ejection of blood from the right ventricle. The patent describes that the system is inflated and deflated in synchrony with the normal heart rhythm, and is designed to reduce the load on the right ventricle to permit healing of injury or defect of the right ventricle. It does not describe or suggest that the proposed regulation of flow into and out of the right ventricle will have an effect on either LVEDV or LVEDP, nor that it could be used to arrest or reverse acute/chronic heart failure.

U.S. Patent Publication No. US 2006/0064059 to Gelfand describes a system and method intended to reduce cardiac infarct size and/or myocardial remodeling after an acute myocardial infarction by reducing the stress in the cardiac walls. The system described in the patent includes a catheter having a proximal portion with an occlusion balloon configured for placement in the inferior vena cava and a distal portion configured for placement through the tricuspid and pulmonary valves into the pulmonary artery. The patent application describes that by partially occluding the inferior vena cava, the system regulates the amount of blood entering the ventricles, and consequently, reduces the load on the ventricles, permitting faster healing and reducing the expansion of the myocardial infarct. The system described in Gelfand includes sensors mounted on the catheter that are read by a controller to adjust regulation of the blood flow entering the heart, and other measured parameters, to within predetermined limits. The patent application does not describe or suggest that the system could be used to treat, arrest or reverse congestive heart failure once the heart has already undergone the extensive remodeling typically observed during patient re-admissions to address the symptoms of congestive heart failure.

U.S. Patent Publication No. US 2010/0331876 to Cedeno describes a system and method intended to treat congestive heart failure, similar in design to described in Gelfand, by regulating the return of venous blood through the inferior vena cava. The system described in Cedeno describes that a fixed volume balloon disposed in the inferior vena cava will limit blood flow in the IVC. The degree of occlusion varies as the vessel expands and contracts during inspiration and expiration, to normalize venous blood return. The patent application further describes that the symptoms of heart failure improve within three months of use of the claimed system. Although the system and methods described in Cedeno appear promising, there are a number of potential drawbacks to such a system that applicants' have discovered during their own research. Applicants have observed during their own research that fully occluding the inferior vena cava not only reduces left ventricular volume, but undesirably also left ventricular pressure, leading to reduced systemic blood pressure and cardiac output. Moreover, full inferior vena cava occlusion may increase venous congestion within the renal, hepatic, and mesenteric veins; venous congestion is a major cause of renal failure in congestive heart failure patients.

There are several major limitations to approaches that involve partial or full occlusion of the inferior vena cava to modulate cardiac filling pressures and improve cardiac function. First, the IVC has to be reached via the femoral vein or via the internal jugular vein. If approached via the femoral vein, then the patient will be required to remain supine and will be unable to ambulate. If approached via the jugular or subclavian veins, the apparatus would have to traverse the superior vena cava and right atrium, thereby requiring cardiac penetration, which predisposes to potential risk involving right atrial injury, induction of arrhythmias including supraventricular tachycardia or bradycardia due to heart block. Second, the IVC approach described by Cedeno and colleagues depends on several highly variable indices (especially in the setting of congestive heart failure): 1) IVC diameter, which is often dilated in patients with heart failure; b) Intermittent (full or partial) IVC occlusion may cause harm by increasing renal vein pressure, which reduces glomerular filtration rates and worsens kidney dysfunction; c) Dependence on the patient's ability to breathe, which is often severely impaired in HF. A classic breathing pattern in HF is known as Cheynes Stokes respiration, which is defined by intermittent periods of apnea where the IVC may collapse and the balloon will cause complete occlusion resulting in lower systemic blood pressure and higher renal vein pressure; d) If prolonged cardiac unloading is required to see a clinical improvement or beneficial changes in cardiac structure or function, then IVC occlusion will not be effective since sustained IVC occlusion will compromise blood pressure and kidney function. Third, the approach defined by Cedeno will require balloon customization depending on IVC size, which may be highly variable. Fourth, many patients with heart failure have IVC filters due to an increased propensity for deep venous thrombosis, which would preclude broad application of IVC therapy.

In view of the foregoing drawbacks of the previously known systems and methods for regulating venous return to address heart failure, it would be desirable to provide systems and methods for treating acute and chronic heart failure that reduce the risk of exacerbating co-morbidities associated with the disease.

It further would be desirable to provide systems and methods for treating acute and chronic heart failure that arrest or reverse cardiac remodeling, and are practical for chronic and/or ambulatory use.

It still further would be desirable to provide systems and methods for treating heart failure that permit patients suffering from this disease to have improved quality of life, reducing the need for hospital admissions and the associated burden on societal healthcare networks.

III. SUMMARY OF THE INVENTION

In view of the drawbacks of the previously known systems and methods for treating heart failure, it would be desirable to provide systems and methods for treating acute and/or chronic heart failure that can arrest, and more preferably, reverse cardiac remodeling that result in the cascade of effects associated with this disease.

It further would be desirable to provide systems and methods for arresting or reversing cardiac remodeling in patients suffering from heart failure that are practical for ambulatory and/or chronic use.

It still further would be desirable to provide systems and methods for treating heart failure that reduce the risk of exacerbating co-morbidities associated with the disease, such as venous congestion resulting in renal and hepatic complications.

It also would be desirable to provide systems and methods for treating heart failure that permit patients suffering from this disease to have improved quality of life, which reducing the need for hospital re-admissions and the associated burden on societal healthcare networks.

These and other advantages are provided by the present disclosure, which provides systems and methods for regulating venous blood return through the superior vena cava ("SVC"), over intervals spanning several cardiac cycles, to reduce ventricular overload. In accordance with the principles of the present disclosure, venous regulation via the SVC can be used to reduce LVEDP, LVEDV, RVEDP, and/or RVEDV, to arrest or reverse ventricular myocardial remodeling. Counter-intuitively, applicants have observed in preliminary animal testing that intermittent partial occlusion of the SVC does not lead to stagnation of cerebral flow or observable adverse side effects. More importantly, applicants' preliminary animal testing reveals that occlusion of the SVC results in significant reduction in both RVEDP and LVEDP, while improving total cardiac output and without a significant impact on left ventricular systolic pressure ("LVSP"). Accordingly, unlike the approach discussed in the foregoing published Cedeno patent application, the present disclosure provides a beneficial reduction in LVEDP, LVEDV, RVEDP, and/or RVEDV, with negligible impact on LVSP, but improved stroke volume (cardiac output), and reduced risk for venous congestion resulting in increased co-morbidities. The systems and methods described herein provide acute improvement in cardiac filling pressures and function to benefit patients at risk for acutely decompensated heart failure.

There are several major advantages to targeting SVC flow (instead of IVC flow). First, device placement in the SVC avoids use of the femoral veins and avoids cardiac penetration. This allows for development of a fully implantable, ambulatory system for acute or chronic therapy. Second, SVC occlusion can be intermittent or prolonged depending on the magnitude of unloading required. Unlike IVC occlusion, prolonged SVC occlusion maintains systemic blood pressure and improves cardiac output. This allows for sustained unloading of both the right and left ventricle, which allows for both acute hemodynamic benefit and the potential for long term beneficial effects on cardiac structure or function. Third, unlike IVC occlusion, SVC occlusion does not depend on patient respiration. Fourth, by developing an internal regulator of SVC occlusion driven by mean right atrial pressure, the SVC device can be programmed and personalized for each patient's conditions. Fifth, by placing the device in the SVC, the device can be used in patients with existing IVC filters.

In accordance with another aspect of the present disclosure, partial intermittent occlusion of the SVC over multiple cardiac cycles is expected to permit the myocardium to heal, such that the reduced wall stress in the heart muscle arrests or reverses the remodeling that is symptomatic of the progression of heart failure. Without wishing to be bound by theory, applicants believe that intermittent occlusion of the SVC permits the heart, when implemented over a period of hours, days, weeks, or months, to transition from a Starling curve indicative of heart failure with reduced ejection fraction towards a Starling curve having LVEDP and LVEDP more indicative of normal cardiac function. Consequently, applicants preliminary animal testing suggests that use of the inventive system over a period of hours, days, weeks, or months, e.g., 3-6 months, may not only arrest the downward spiral typical of the disease, but also may enable the heart to recover function sufficiently for the patient to terminate use of either the system of the present disclosure, pharmaceutical treatments, or both.

In accordance with another aspect of the disclosure, a system is provided that comprises a catheter having an flow limiting element configured for placement in the SVC, and a controller for controlling actuation of the flow limiting element. The controller is preferably programmed to receive an input indicative of fluctuations in the patient's hemodynamic state resulting from the patient's ambulatory activity, and to regulate actuation of the flow limiting element responsive to that input. The controller may be programmed at the time of implantation of the catheter to retain full or partial occlusion of the SVC over a predetermined number of heart cycles or predetermined time interval based on the patient's resting heart rate, and this preset number of cycles or time interval may be continually adjusted by the controller responsive to the patient's heart rate input. The controller may further receive signals from sensors and/or electrodes indicative of sensed parameters reflecting the hemodynamic state, e.g., blood flow rate, blood volume, pressure including cardiac filling pressure, and the controller may continually adjust the preset number of cycles or time interval responsive to the sensed parameter(s).

In one preferred embodiment, the catheter is configured to be implanted via the patient's left subclavian vein, so that the flow limiting element is disposed in the SVC just proximal of the right atrium. A proximal end of the catheter may be coated or impregnated with an antibacterial agent to reduce infection at the site where the catheter passes transcutaneously. The controller preferably is battery-powered, and includes a quick-connect coupling that permits the actuation mechanism of the controller to operatively couple to the flow limiting element. In a preferred embodiment, the controller is sufficiently small that it may be worn by the patient in a harness around the shoulder. In contrast to previously-known systems, which tether the patient to a bed or acute-care setting, the system of the present disclosure is configured so that the patient is ambulatory and can go about most daily activities, thereby enhancing the patient's quality-of-life and improving patient compliance with the course of treatment using the inventive system. In one embodiment, the controller is configured for implantation at a suitable location within the patient, e.g., subcutaneously under the clavicle. In such an embodiment, the implantable controller is configured for bidirectional communication with an external controller, e.g., mobile device or system-specific device. The external controller may be configured to charge the battery of the implantable controller, e.g., via respective inductive coils in each controller, and may receive data indicative of the sensed parameters including heart rate, blood flow rate, blood volume, pressure including cardiac filling pressure.

In a preferred embodiment, the flow limiting element comprises a non-compliant or semi-compliant balloon affixed to a distal region of the catheter, such that the controller actuates the balloon by periodically inflating and deflating the balloon to selectively fully or partially occlude the SVC. In alternative embodiments, the flow limiting element may comprise a membrane covered umbrella, basket or other mechanical arrangement capable of being rapidly transitioned between deployed and contracted positions, e.g., by a driveline connected to the controller. In still further embodiments, the flow limiting element may take the form of a butterfly valve or ball valve, provided the flow limiting element does not create stagnant flow zones in the SVC when in the contracted or open position.

The inventive system may include a sensor disposed on the catheter for placement within the venous vasculature to measure the patient's heart rate or blood pressure. The sensor preferably generates an output signal that is used as an input to the controller to adjust the degree or timing of the occlusion created by the flow limiting element. In another embodiment, the controller may be configured to couple to a third-party heart rate sensor, such as those typically used by sporting enthusiasts, e.g., the Fitbit, via available wireless standards, such as Bluetooth, via the patient's smartphone. In this embodiment, the cost, size and complexity of the controller may be reduced by integrating it with commercially available third-party components.

In accordance with another aspect of the disclosure, a method for controlling blood flow in a patient comprises inserting and guiding to the vena cava of a patient a venous occlusion device, coupling the occlusion device to a controller worn externally by, or implanted in, the patient; and activating the venous occlusion device intermittently, for intervals spanning multiple cardiac cycles, so that over a period of several minutes, hours, days, weeks, or months, remodeling of the myocardium is arrested or reversed.

IV. BRIEF DESCRIPTION OF THE DRAWINGS

The characteristics and advantages of the present disclosure will become apparent from the detailed description of the embodiment of the disclosure presented below in conjunction with the attached drawings, in which:

FIGS. 8A and 8B are schematic drawings of an flow limiting element comprising a round ball-shaped balloon shown in its expanded and contracted states, respectively.

FIGS. 9A and 9B are schematic drawings of an flow limiting element comprising a spring-loaded plug shown in its expanded and contracted states, respectively.

FIGS. 10A and 10B are schematic drawings of an flow limiting element comprising an alternative embodiment of a spring-loaded plug shown in its expanded and contracted states, respectively.

V. DETAILED DESCRIPTION OF THE INVENTION

Figure 1A:
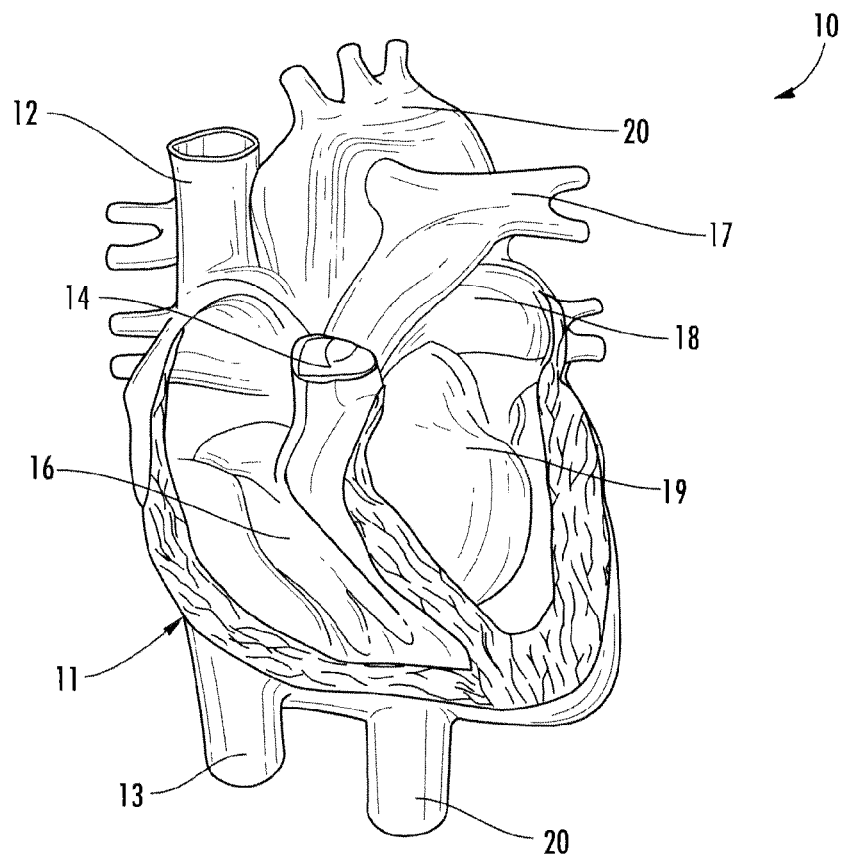
FIG. 1A is a frontal, partially broken-away view of the major arteries and veins of the heart.
Figure 1B:
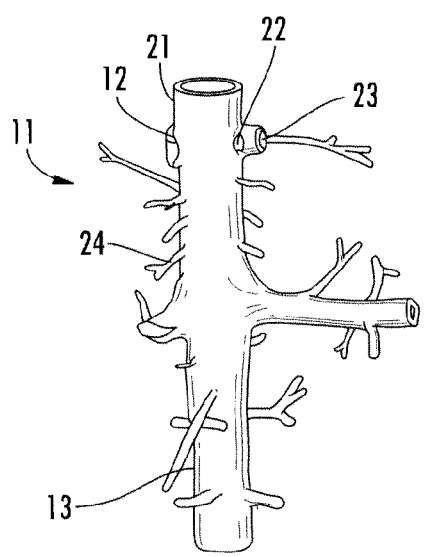
FIG. 1B illustrates the vena cava including major veins associated with the vena cava.

Referring to FIGS. 1A and 1B, the human anatomy in which the present disclosure is designed for placement and operation is described as context for the system and methods of the present disclosure.

More particularly, referring to FIG. 1A, deoxygenated blood returns to heart 10 through vena cava 11, which comprises superior vena cava 12 and inferior vena cava 13 coupled to right atrium 14 of the heart. Blood moves from right atrium 14 through tricuspid valve 15 to right ventricle 16, where it is pumped via pulmonary artery 17 to the lungs. Oxygenated returns from the lungs to left atrium 18 via the pulmonary vein. The oxygenated blood then enters left ventricle 19, which pumps the blood through aorta 20 to the rest of the body.

As shown in FIG. 1B, superior vena cava 12 is positioned at the top of vena cava 11, while inferior vena cava 13 is located at the bottom of the vena cava. FIG. 1B also shows some of the major veins connecting to the vena cava, including right hepatic vein 21, middle hepatic vein 22, left hepatic vein 23 and suprarenal vein 24. As noted above, occlusion of the inferior vena cava 13 may pose risks of venous congestion, and in particular, potential blockage or enlargement of the hepatic veins and/or suprarenal vein that may worsen, rather than improve, the patient's cardiovascular condition and overall health.

In accordance with one aspect of the present disclosure, applicants have determined that selective intermittent occlusion of the superior vena cava ("SVC") poses fewer potential adverse risks that occlusion of the inferior vena cava ("IVC"). Moreover, applicants' preliminary animal testing reveals that controlling the return of venous blood to the right ventricle by partially or fully occluding the SVC beneficially lowers RVEDP, RVEDV, LVEDP and LVEDV without adversely reducing left ventricular systolic pressure (LVSP), as was observed when occluding the IVC in applicants' animal model.

Applicants expect that selective intermittent occlusion of the SVC position will reduce the risk of worsening congestion of the kidneys, which is a major cause of 'cardio-renal' syndrome, as compared to IVC occlusion. Cardio-renal syndrome is impaired renal function due to volume overload and neurohormonal activation in patients with heart failure. In addition, implantation in the SVC permits a supra-diaphragmatic device implant that could not be used in the IVC without cardiac penetration and crossing the right atrium. Further, implantation of the occluder in the SVC avoids the need for groin access as required by IVC implantation, which would limit mobility making an ambulatory device impractical for short term or long term use. In addition, minor changes in IVC occlusion (time or degree) may cause more dramatic shifts in preload reduction and hence total cardiac output/systemic blood pressure whereas the systems and methods of the present disclosure as expected to permit finely tuned decrease in venous return (preload reduction), While not wishing to be bound by theory, it is applicants' expectation that their proposed system and method for regulating venous blood return, if implemented over a period of hours, days, weeks, or months, will beneficially permit a patients' heart to arrest or recover from remodeling of the myocardium. Applicants' preliminary animal testing indicates that the system enables the myocardium to transition from pressure-stroke volume curve indicative of heart failure towards a pressure-stroke volume curve more closely resembling that of a healthy heart.

In general, the system and methods of the present disclosure may be used to treat any disease to improve cardiac function by arresting or reversing myocardial remodeling, and particularly those conditions in which a patient suffers from heart failure. Such conditions include but are not limited to, e.g., systolic heart failure, diastolic (non-systolic) heart failure, decompensated heart failure patients in (ADHF), chronic heart failure, acute heart failure. The system and methods of the present disclosure also may be used as a prophylactic to mitigate the aftermath of acute right or left ventricle myocardial infarction, pulmonary hypertension, RV failure, post-cardiotomy shock, or post-orthotopic heart transplantation (OHTx) rejection.

The relationship between left ventricular pressure or left ventricular volume and stroke volume is often referred to as the Frank-Starling relationship, or "Starling curve." That relationship states that cardiac stroke volume is dependent on preload, contractility, and afterload. Preload refers to the volume of blood returning to the heart; contractility is defined as the inherent ability of heart muscle to contract; and afterload is determined by vascular resistance and impedance. In heart failure due to diastolic or systolic dysfunction, reduced stroke volume leads to increased volume and pressure increase in the left ventricle, which can result in pulmonary edema. Increased ventricular volume and pressure also results in increased workload and increased myocardial oxygen consumption. Such over-exertion of the heart results in worsening cardiac function as the heart becomes increasingly deprived of oxygen due to supply and demand mismatch. Furthermore, as volume and pressure build inside the heart, contractile function worsens due to stretching of cardiac muscle. This condition is termed 'congestive heart failure'.

Figure 2:
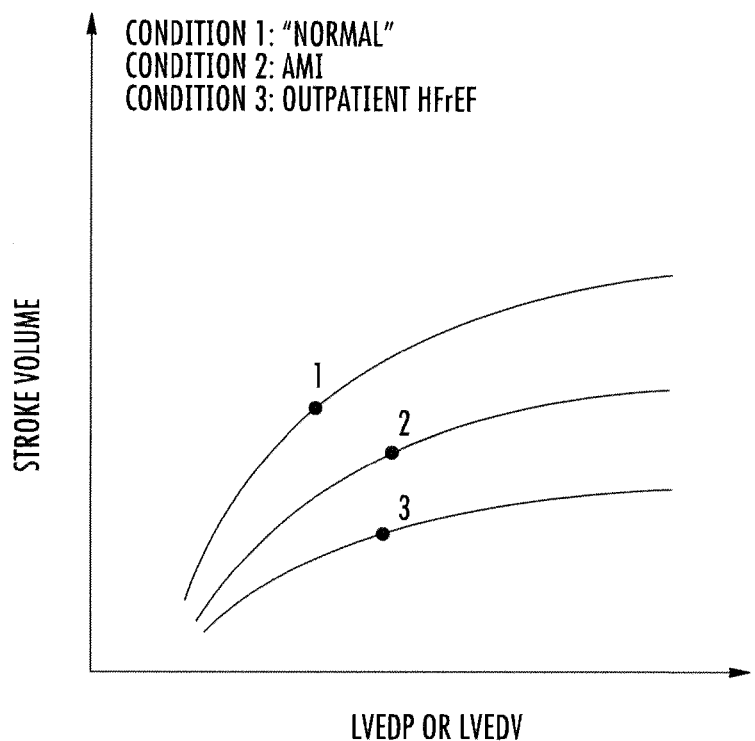
FIG. 2 is a graph illustrating the Frank-Starling curve for normal and afflicted cardiac conditions.

Referring to FIG. 2, a series of Starling curves are illustrated, in which topmost curve (curve 1) depicts functioning of a normal heart. As shown in the curve, stroke volume increases with increasing LVEDP or LVEDV, and begins to flatten out, i.e., the slope of the curve decreases, only at very high pressures or volumes. A patient who has just experienced an acute myocardial infarction ("AMI"), as indicated by the middle curve (curve 2), will exhibit reduced stroke volume at every value of LVEDV or LVEDP. However, because the heart has just begun to experience the overload caused by the localized effect of the infarct, myocardial contractility of the entire ventricle is still relatively good, and stroke volume is still relatively high at low LVEDP or LVEDV. By contrast, a patient who has suffered from cardiac injury in the past may experience progressive deterioration of cardiac function as the myocardium remodels over time to compensate for the increased workload and reduced oxygen availability, as depicted by the lowermost curve (curve 3) in FIG. 2. As noted above, this can lead to progressively lower stroke volume as the ventricle expands due to generally higher volume and pressure during every phase of the cardiac cycle. As will be observed from comparison of curves 1 and 3, the stroke volume continues to decline as the LVEDP or LVEDV climb, until eventually the heart gives out or the patient dies of circulatory-related illness.

Figure 3:
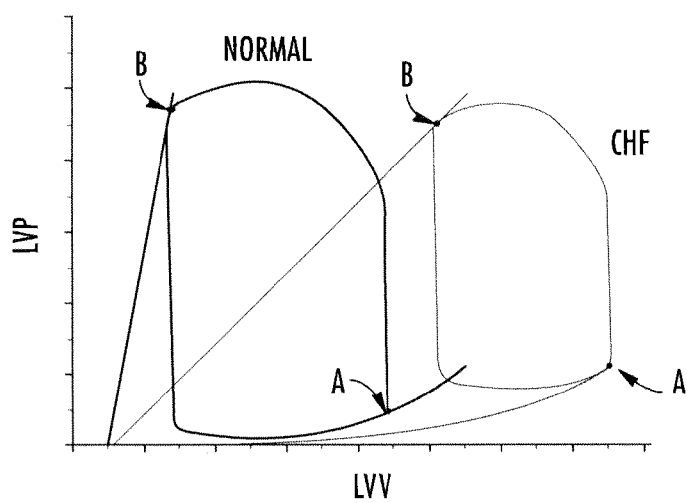
FIG. 3 is a graph of exemplary pressure-volume loop curves of left ventricular pressure versus left ventricular volume throughout a cardiac cycle for a patient having normal cardiac function and a patient suffering from congestive heart failure.

FIG. 3 illustratively shows pressure-volume loops for a normal heart, labeled "normal", corresponding to curve 1 in FIG. 2, and a heart suffering from congestive heart failure, labeled "CHF" (curve 3 in FIG. 2). For each loop, the ventricular volume and pressure at the end of diastole correspond to the lower-most, right-most corner of the loop (point A), while the upper-most, left-most corner of each loop corresponds to the beginning systole (point B). The stroke volume for each pressure-volume loop corresponds to the area enclosed within the loop. Accordingly, the most beneficial venous regulation regime is one that reduces the volume and pressure at point A while not also causing negligible reduction in point B, thereby maximizing the stroke volume.

In accordance with one aspect of the present disclosure, the system and methods of the present disclosure are designed, over the course of hours, days, weeks, or months, to shift or transition the Starling curve of the patient's heart leftwards on the diagram of FIG. 2 (or to move the pressure-volume loop in FIG. 3 leftwards and downwards). This may be accomplished by intermittently fully or partially occluding the SVC to reduce the volume and hence pressure of blood entering the right ventricle, and which must then be pumped by the left ventricle. Applicants' preliminary animal testing indicates that such intermittent occlusion, maintained over several cardiac cycles, reduces the workload and wall stress in the myocardium throughout the cardiac cycle, reduces myocardial oxygen consumption, and improves contractile function. See also, FIGS. 13 and 14 discussed below.

Figure 4:
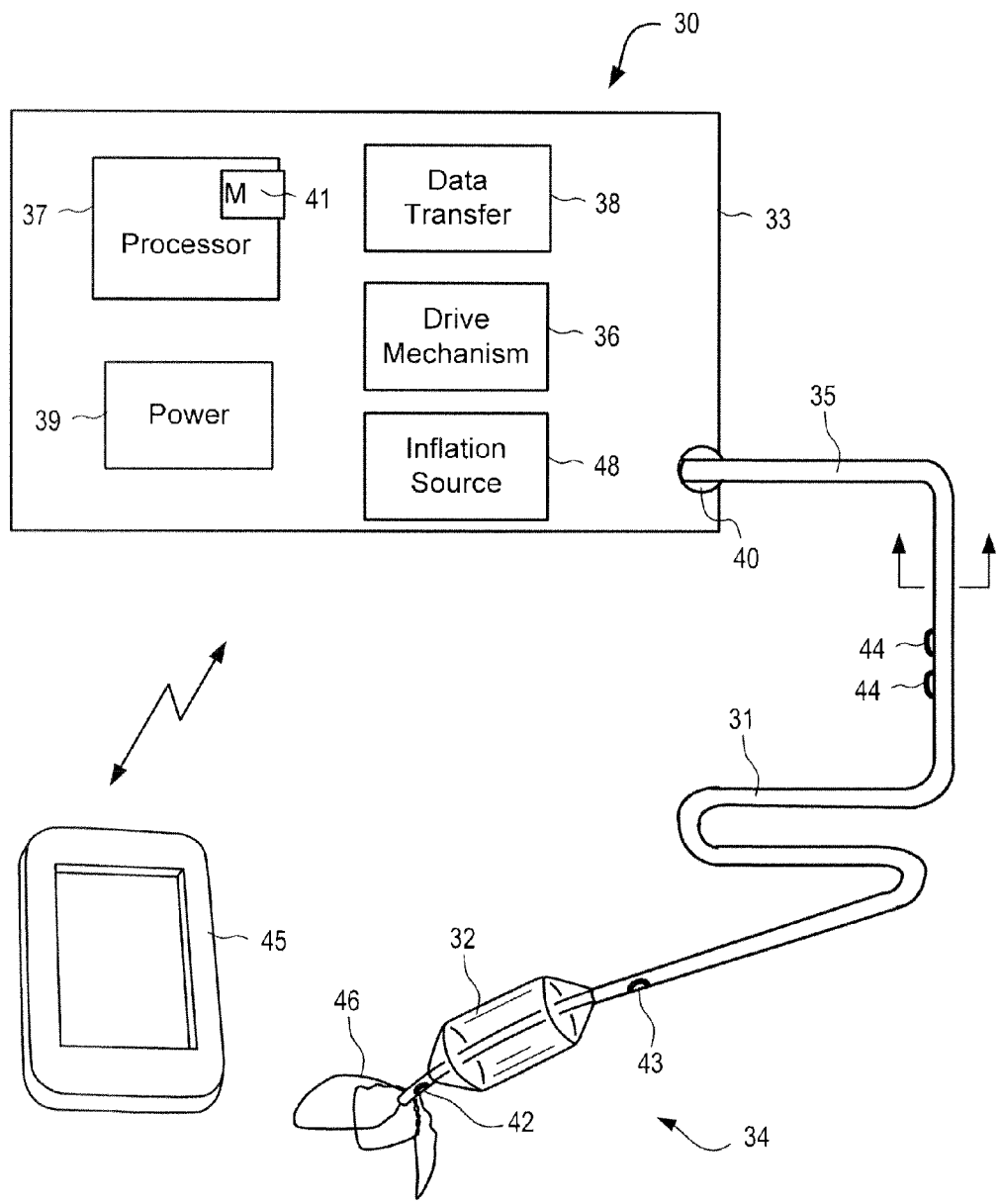
FIG. 4 is a schematic drawing of a system constructed in accordance with the principles of the present disclosure.

Referring now to FIG. 4, exemplary system 30 of the present disclosure is described. System 30 includes catheter 31 having flow limiting element 32 coupled to controller 33 programmed to intermittently actuate flow limiting element 32. As discussed below, system optionally may be configured to transfer information bi-directionally with conventional computing device 45 such as a smartphone, laptop, smartwatch, or tablet, illustratively an Apple iPhone 5 or iPad, available from Apple Inc., Cupertino, Calif., on which a special-purpose application has been installed to communicate and/or control controller 33.

Preferably, catheter 31 comprises a flexible tube having distal portion 34 configured for placement in the SVC. Distal portion 34 includes flow limiting element 32 that, in use, is disposed in superior vena cava 12 (see FIG. 2) of a patient to selectively impede blood flow into right atrium 14. In this embodiment, flow limiting element 32 illustratively comprises a balloon capable of transitioning between a contracted state, allowing transluminal placement and an expanded, deployed state. Flow limiting element 32 preferably is sized and shaped so that it partially or fully occludes flow in the SVC in the expanded state. Catheter 31 is coupled at proximal end 35 to controller 33, which houses drive mechanism 36 (e.g., motor, pump) for actuating flow limiting element 32, processor 37 programmed to control signals to drive mechanism 36, and optional sensor 38 for monitoring a physiologic parameter of the patient, such as heart rate or blood pressure.

Controller 33 may include source of inflation medium 48 (e.g., gas or fluid) and drive mechanism 36 may transfer the inflation medium between the source and flow limiting element 32 responsive to commands from processor 37. When flow limiting element 32 is inflated with inflation medium, it partially or fully occludes venous blood flow through the SVC; when the inflation medium is withdrawn, flow limiting element 32 deflates to remove the occlusion, thereby permitting flow to resume in the SVC. Flow limiting element 32 may be a balloon that preferably comprises a compliant or semi-compliant material, e.g., nylon, which permits the degree of expansion of the balloon to be adjusted to effectuate the desired degree of partial or complete occlusion of the SVC. In addition, catheter 31, when partially external, provides a failsafe design, in that flow limiting element 32 only can be inflated to provide occlusion when the proximal end of catheter 31 is coupled to controller 33. Such a quick-disconnect coupling 40 at proximal end 35 permits the catheter to be rapidly disconnected from controller 33 for cleaning and/or emergency.

Controller 33 preferably also includes power supply 39 (e.g., battery) that provides the power needed to operate processor 37, drive mechanism 36 and data transfer circuit sensor 38. Controller 33 preferably is sized and of such a weight that it can be worn in a harness under the patient's clothing, so that the system can be used while the patient is ambulatory or such that controller 33 may be implanted within the patient. As discussed herein below, processor 37 includes memory 41 for storing computer software for operating the controller 33.

Controller 33 also may be configured for implantation at a suitable location within the patient, e.g., subcutaneously under the clavicle. In such an embodiment, the implantable controller is configured for bidirectional communication with an external controller, e.g., computing device 45 or system-specific device. The external controller may be configured to charge the battery of the implantable controller, e.g., via respective inductive coils in or coupled to each controller, and may receive data indicative of the sensed parameters resulting from the patient's ambulatory activity including heart rate, blood flow rate, blood volume, pressure including cardiac filling pressure.

In one embodiment, data transfer circuit 38 monitors an input from an external sensor, e.g., positioned on catheter 31, and provides that signal to processor 37. Processor 37 is programmed to receive the input from data transfer circuit 38 and adjust the interval during which flow limiting element 32 is maintained in the expanded state, or to adjust the degree of occlusion caused by flow limiting element 32. Thus, for example, catheter 31 may have optional sensor 42 positioned within distal region 34 of the catheter to measure parameters, e.g., heart rate, blood flow rate, blood volume, pressure including cardiac filling pressure and central venous pressure. The output of sensor 42 is relayed to data transfer circuit 38 of controller 33, which may pre-process the input signal, e.g., decimate and digitize the output of sensor 42, before it is supplied to processor 37. The signal provided to processor 37 allows for assessment of the effectiveness of the flow limiting element, e.g., by showing reduced venous pressure during occlusion and during patency, and may be used for patient or clinician to determine how much occlusion is required to regulate venous blood return based on the severity of congestion in the patient. Additionally, sensor 43 may be included on catheter 31 proximal to flow limiting element 32, to measure parameters, e.g., heart rate, blood flow rate, blood volume, pressure including cardiac filling pressure and central venous pressure. Sensor 43 may be used to determine the extent of occlusion caused by element 32, for example, by monitoring the pressure drop across the flow limiting element.

As another example, catheter 31 may include electrodes 44 for sensing the patient's heart rate. It is expected that it may be desirable to adjust the interval during which occlusion of the SVC is maintained responsive to the patient's ambulatory activities, which typically will be reflected in the patient's hemodynamic state by a sensed physiological parameter(s), e.g., heart rate, blood flow rate, blood volume, pressure including cardiac filling pressure and/or central venous pressure. Accordingly, electrodes 44 may provide a signal to data transfer circuit 38, which in turn processes that signal for use by the programmed routines run by processor 37. For example, if the occlusion is maintained for a time programmed during initial system setup to reflect that the patient is resting, e.g., so that flow limiting element is deployed for 5 seconds and then released for two seconds before being re-expanded, it may be desirable to reduce that the occluded time interval to 4 seconds or more depending upon the level of physical activity of the patient, as detected by a change in heart rate, blood flow rate, blood volume, pressure including cardiac filling pressure and/or central venous pressure above or below predetermined thresholds. Alternatively, processor 37 may be programmed to maintain partial or full occlusion in the SVC for a preset number of cardiac cycles determined at the time of initial implantation of the catheter. Sensor inputs provided to data transfer circuit 38, such as hemodynamic state, also may be used to adjust the duty cycle of the flow limiting element responsive to the patient's detected level of activity. In addition, processor 37 may be programmed to maintain partial or full occlusion in the SVC for a preset number of cardiac cycles after adjustment to the predetermined occlusion interval is made.

Data transfer circuit 38 also may be configured to provide bi-directional transfer of data, for example, by including wireless circuitry to transfer data from controller 33 to an external unit for display, review or adjustment. For example, data transfer circuit may include Bluetooth circuitry that enables controller 33 to communicate with patient's computing device 45. In this manner, controller may send information regarding functioning of the system directly to computing device 45 for display of vital physiologic or system parameters using a suitably configured mobile application. In addition, the patient may review the data displayed on the screen of computing device 45 and determine whether he or she needs to seek medical assistance to address a malfunction or to adjust the system parameters. Further, the mobile application resident on computing device 45 may be configured to automatically initiate an alert to the clinician's monitoring service via the cellular telephone network.

Optionally, data transfer circuit 38 may be configured to synchronize to receive data from other mobile applications on computing device 45, and thus reduce the cost and complexity of the inventive system. For example, a number of third party vendors, such as Fitbit, Inc., San Francisco, Calif., market monitors that measure physiologic parameters in real time, such as the Charge HR wristband monitor, that measures physical activity and heart rate. In accordance with one aspect of the disclosure, data transfer circuit 38 can be programmed to receive an input from such a third-party monitor via wireless communication with computing device 45, and that processor 37 may be programmed to control activation of drive mechanism 36 responsive to that input. In this embodiment, the catheter need not include optional sensor 42, sensor 43 or electrodes 44, thereby greatly simplifying the construction of catheter 31 and coupling 40.

Catheter 31 may include anchor member 46 configured to anchor flow limiting element 32 within the SVC. Anchor member 46 may be contractable for delivery in a contracted state and expandable upon release from a delivery device, e.g., a sheath. Anchor member 46 may be coupled to catheter proximal or distal to flow limiting element 32 and/or may be coupled to flow limiting element 32.

Figure 5A:
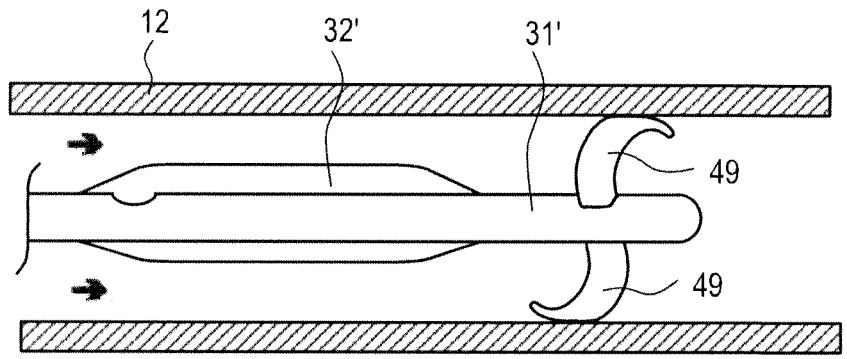
FIGS. 5A-5B are schematic drawings of the catheter of FIG. 4 wherein the flow limiting element comprises a cylindrical balloon with modified anchoring members shown in its expanded and contracted states, respectively.
Figure 5B:
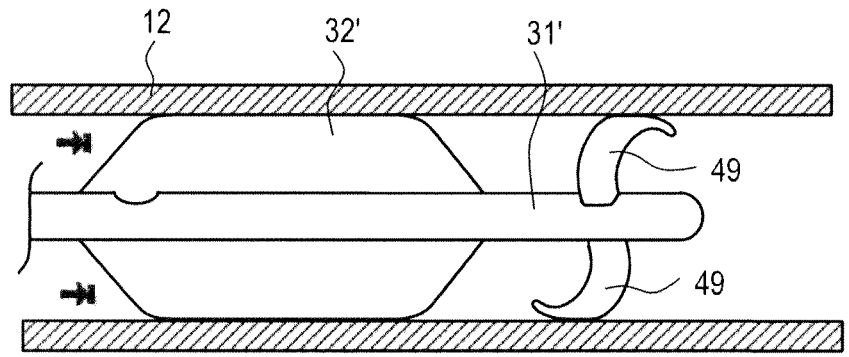

Referring now to FIGS. 5A and 5B, an exemplary embodiment of catheter 31' is described, wherein catheter 31' is constructed similarly to catheter 31 of FIG. 4 except with a modified anchor. As shown in FIG. 5A when flow limiting element 32' is in an expanded, fully occluding state, and shown in FIG. 5B, when flow limiting element 32' is in a contracted state, catheter 31' may include radially expanding anchoring arms 49. Anchoring arms 49 are configured to radially expand, e.g., when exposed from a delivery sheath, to contact the inner wall of superior vena cava 12 and anchor flow limiting element 32' therein.

Figure 6:
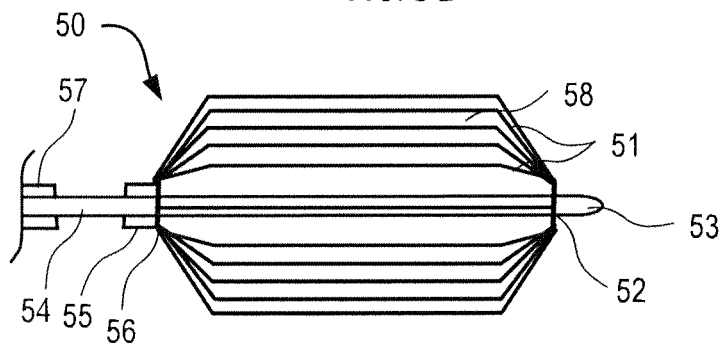
FIG. 6 is a schematic drawing of the catheter of FIG. 4 wherein the flow limiting element comprises a mechanically actuated membrane covered basket.

Referring now to FIG. 6, an alternative embodiment is described wherein the occlusion may comprise a wire basket. Flow limiting element 50 may be formed of a biocompatible material, such as nickel-titanium or stainless steel, and comprises plurality of axially or spirally extending wires 51 that are biased to expand radially outward when compressed. Flow limiting element 50 preferably includes a biocompatible membrane covering, so that it partially or fully occludes flow in the SVC in the expanded state. Wires 51 may be coupled at distal end 52 to distal end 53 of actuation wire 54, and affixed to ring 55 at their proximal ends 56. Ring 55 is disposed to slide on actuation wire 54 so that when actuation wire 54 is pulled in the proximal direction against sheath 57 (see FIGS. 5A and 5B), wires 51 expand radially outward. As shown in FIG. 5B, in response to a force applied to the proximal end of actuation wire 54 by drive mechanism 36, actuation wire 54 is retracted proximally against sheath 57 of the catheter; transitioning flow limiting element 50 to its expanded deployed state. Conversely, when drive mechanism 36 is deactivated, spring force applied by wires 51 pulls actuation wire 54 in the proximal direction, thereby enabling wires 51 to return to their uncompressed state, lying substantially flat against actuation wire 54. As noted above, flow limiting element 50 has a "fail safe" design, so that the flow limiting element resumes the collapsed, contracted state shown in FIG. 5A when catheter 31 is uncoupled from drive mechanism 36. In this embodiment, drive mechanism 36 may be a motor, which may be a linear motor, rotary motor, solenoid-piston, or wire motor.

Flow limiting element 50 may be constructed so that it is biased to the contracted position when catheter 31 is disconnected from controller 33, so that flow limiting element 50 can only be transitioned to the expanded, deployed state when the catheter is coupled to controller 33 and the processor has signaled drive mechanism 36 to expand the flow limiting element.

Referring still to FIG. 6, flow limiting element 50 preferably includes a sheer biocompatible elastic membrane 58 disposed on wires 51, such as expanded polytetrafluoroethylene (ePTFE), which occludes blood flow through the SVC when the flow limiting element is in the expanded deployed state. A suitable ePTFE material can be obtained, for example, from W. L. Gore & Associates, Inc., Flagstaff, Ariz.

Figure 7:
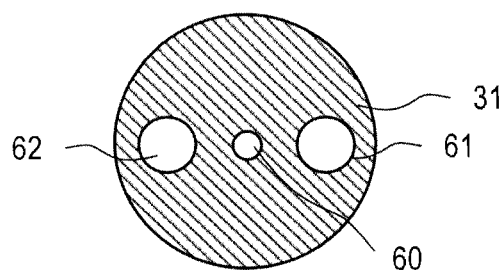
FIG. 7 is a cross-sectional view of the catheter of FIG. 4.

Referring now to FIG. 7, catheter 31 preferably includes at least three lumens 60, 61, 62. Lumen 60 may be used as an inflation lumen (FIGS. 4-5B) and/or for carrying actuation wire 54 (FIG. 6) that extends between flow limiting element 50 and the drive mechanism 36 of controller 33. Lumen 61 permits optional sensors 42, 43 or electrodes to communicate with data transfer circuit 38, and optional lumen 62 for delivering a pharmacological agent (e.g., a drug) to the heart.

In operation, catheter 31 with flow limiting element 32/50 is inserted into the patient's subclavian vein and guided to the SVC of the patient, e.g., to a position proximal of the entrance to the right atrium (see FIG. 1A). Techniques known in the art can be used to insert and fix flow limiting element 32/50 at the desired venous location in the patient. Proper localization of the device may be confirmed using, for example, vascular ultrasound. Alternatively, flow limiting element 32/50 may be inserted through the jugular vein and guided to the SVC under fluoroscopic or ultrasound guidance.

Once catheter 31 and flow limiting element 32/50 are positioned at the desired locations, controller 33 initiates a process in which the occlusion element is expanded and contracted such that blood flow in the SVC is intermittently occludes and resumed. The extent to which the flow limiting element impedes blood flow can be regulated by adjusting the degree to which the flow limiting element expands radially, and also for time interval for the occlusion, e.g., over how many heart beats. For example, in some embodiments the flow limiting element may impede blood flow in the SVC by anywhere from at least 50% up to 100%. Impedance of blood flow may be confirmed using methods known in the art, e.g., by measuring reductions in pressure or visually using ultrasound.

In accordance with one aspect of the disclosure, controller 33 includes software stored in memory 41 that controls the timing and duration of the successive expansions and contractions of flow limiting element 32/50. As described above, the programmed routines run by processor 37 may use as an input the patient's cardiac cycle. For example, in some embodiments, the software may be configured to actuate flow limiting element 50 to maintain partial or complete occlusion of the SVC over multiple cardiac cycles, for example, four or more successive heart beats in the subject. Controller 33 may accept as input via data transfer circuit 38 an output of electrodes 44 representative of the patient's electrocardiogram (ECG), or alternatively may receive such an input wirelessly from a third-party heart rate application running on the patient's smartphone, such that the software running on processor 37 can adjust the interval and/or degree of the occlusion provided by system 30 responsive to the patient's heart rate. Thus, for example, if the patient is physically active, the timing or degree of occlusion caused by the flow limiting element may be reduced to permit faster replenishment of oxygenated blood to the patient's upper extremities. Conversely, if the heart rate indicates that the patient is inactive, the degree of occlusion of the SVC may be increased to reduce the resting workload on the heart. Alternatively or in addition, system 30 may accept an input via data transfer circuit 38 a value, measured by optional sensors 42 and 43, or a third party application and device, such as a blood pressure cuff, representative of the patient's blood pressure, such that controller 37 regulates flow through the SVC responsive to the patient's blood pressure.

Controller 33 may be programmed to cause the flow limiting element (from FIGS. 4, 5A, 5B, 6, 8A-10B) to expand when a sensed parameter is outside a predetermined range and/or above or below a predetermined threshold. For example, controller 33 may cause the flow limiting element to expand when right atrium ("RA") pressure is sensed by optional sensors 42 and/or 43 to be within a predetermined range, e.g., 15 to 30 mmHg, 18 to 30 mmHg, 20 to 30 mmHg, 20 to 25 mmHg, or above a predetermined threshold, e.g., 15 mmHg, 18 mmHg, 20 mmHg, 22 mmHg, 25 mmHg, 30 mmHg. As another example, controller 33 may cause the flow limiting element to expand when the mean pulmonary artery ("PA") pressure is sensed by optional sensors 42 and/or 43 to be within a predetermined range, e.g., 15 to 30 mmHg, 18 to 30 mmHg, 20 to 30 mmHg, 20 to 25 mmHg, or above a predetermined threshold e.g., 15 mmHg, 18 mmHg, 20 mmHg, 22 mmHg, 25 mmHg, 30 mmHg. The predetermined range and/or the predetermined threshold may be patient specific and controller 33 may be programmed and reprogrammed for individual patients.

Referring now to FIGS. 8-10, alternative forms of intravenous flow limiting elements suitable for use to occlude the SVC are described. As will be apparent to one skilled in the art, while FIGS. 4-6 depict a cylindrical flow limiting element, other shapes may be used. In addition, while not illustrated with anchoring members in FIGS. 8-10, anchoring members may be included. In each pair of drawings, 8A, 8B, 9A, 9B and 10A, 10B, the pair-wise drawings depict that each flow limiting element has a collapsed contracted state (FIGS. 8A, 9A and 10A), where the flow limiting element does not significantly impede blood flow, and an expanded deployed state (FIGS. 8B, 9B and 10B), in which the flow limiting element partially of fully occludes blood flow through the SVC.

In particular, referring to FIGS. 8A and 8B, catheter 70 includes balloon 71 attached to distal end 72. Balloon 71 is illustrated as having a rounded ball shape.

Referring now to FIGS. 9A and 9B, catheter 80 includes flow limiting element 81 comprising spring-loaded plug 82 formed of a biocompatible material (e.g., beryllium) and having a tapered conical shape. Spring-loaded plug 82 is captured in its collapsed contracted state within sheath 83 disposed at distal end 84 of catheter 80. More particularly, a vertex of conically-shaped plug 82 is positioned adjacent the proximal end 85 of sheath 83. During delivery of catheter 80, spring-loaded plug 82 is captured within sheath 83 in its low-profile state to allow blood flow in the SVC. To expand spring-loaded plug 82, force is applied via actuation wire 86 to withdraw plug 82 from sheath 83. As for the previous embodiments, plug 82 is biased to return within sheath 83 when the proximal force is removed from the proximal end of actuation wire 86, so that the flow limiting element 82 remains in its collapsed contracted state if disconnected from controller 33.

Referring to FIGS. 10A and 10B, catheter 90 depicts a further alternative embodiment of occlusive device 91, which takes the form of spring-loaded plug 92. Spring-loaded plug 92 is similar to plug 82 of FIGS. 9A and 9B, and has a tapered conical shape and is loaded within sheath 93 disposed at distal end 94 of catheter 90. In response to a distally-directed force applied by drive mechanism 36 to the proximal end of catheter 90, spring-loaded plug 92 is pushed out of distal end of sheath 94 and expands to occlude the SVC. When the distally-directed force is removed, spring-loaded plug 92 retracts to its collapsed contracted state within sheath 94, thereby permitting blood to flow substantially unimpeded through the SVC.

Applicants have observed that preliminary animal resting indicates that a system constructed and operated in accordance with the methods of the present disclosure provides significant benefits over previously-known systems for treating heart failure. Results of such preliminary testing conducted on swine models one week post myocardial infarction are described below.

Figure 11:
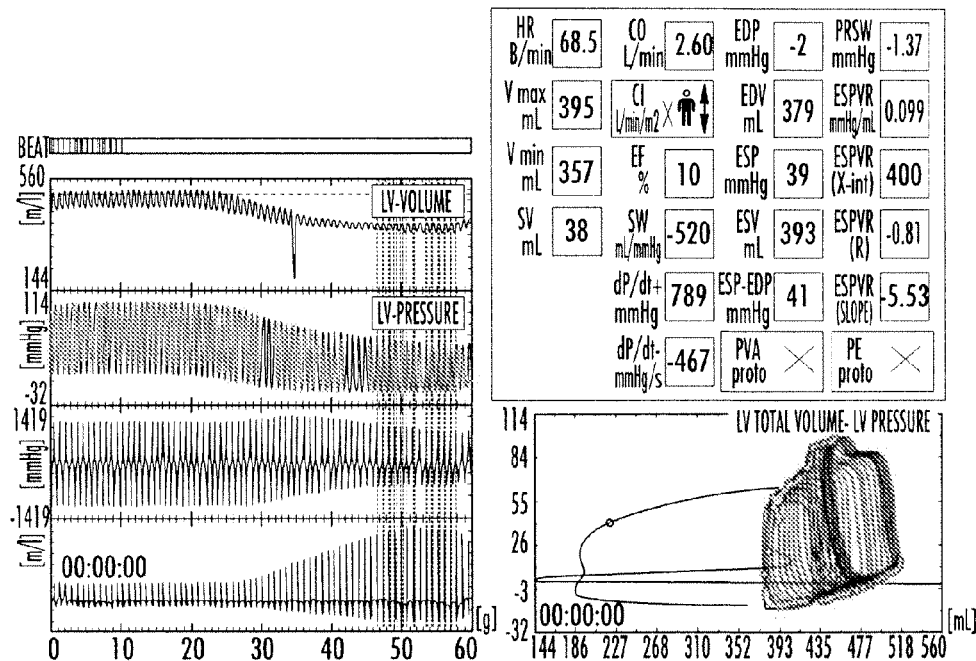
FIG. 11 is a graph showing the changes in left ventricle systolic and diastolic pressures, LV volume, and aortic pressure as a function of time following occlusion of either the inferior vena cava (IVC) or the superior vena cava (SVC) in a swine subjected to heart failure in accordance with the principles of the present disclosure.

Referring to FIG. 11, simultaneous LV pressure and volume and Aortic pressure measurements are shown across 40-50 successive heart beats in a swine model of heart failure following either full occlusion of the inferior vena cava (IVC; FIGS. 11 A and B) as suggested in the foregoing published Cedeno patent application or full occlusion of the superior vena cava (SVC; FIGS. 11 C and D). Left ventricular end diastolic pressure corresponds to lower right-hand corner of the pressure-volume loop and left ventricular systolic pressure corresponds to upper left-hand corner of the pressure-volume loop in FIGS. 11A and 11C. Within this brief period of time, IVC occlusion rapidly and decreased LV pressure, volume, and aortic pressure to critically low values with potentially dangerous consequences to the patient (FIGS. 11 A and B). Compared to IVC occlusion, across the same time period, SVC occlusion marginally decreased LV systolic pressure and aortic pressures, but significantly decreased LV diastolic pressure, which is the primary marker of congestive heart failure (FIGS. 11 C and D). These findings indicate that SVC occlusion may provide a superior approach to reducing LV filling pressures without detrimental effects to systemic blood pressure.

Figure 12:
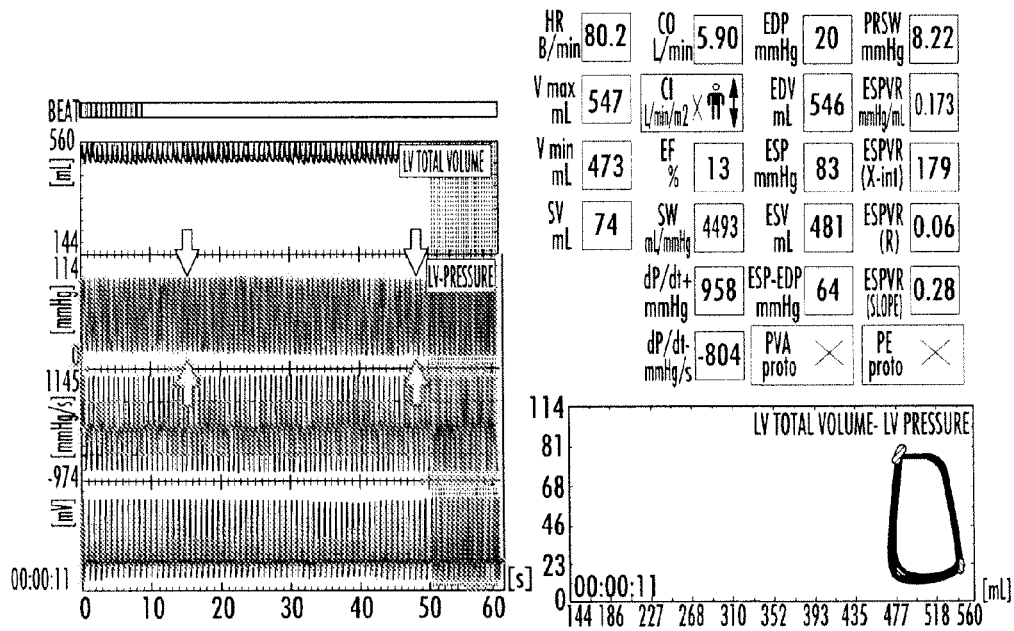
FIG. 12 are hemodynamic tracings showing the changes in pulmonary artery and renal vein pressures as a function of time following occlusion of either the inferior vena cava (IVC) or the superior vena cava (SVC) in a swine subjected to heart failure in accordance with the principles of the present disclosure.

Referring to FIG. 12, as noted above, IVC occlusion increased renal vein pressure from 5 mmHg to 15 mmHg within the 30-40 seconds of occlusion (FIG. 12A). After 2 minutes peak renal vein pressure was 23 mmHg. In contrast, SVC occlusion did not affect renal vein pressure across any time period studied (FIG. 12B). These findings suggest that IVC occlusion may result in congestion of the renal and hepatic veins, which could give rise to exacerbate, rather than ameliorate, complications often associated with congestive heart failure including liver and kidney failure.

Advantageously, the method of the present disclosure of partially occluding the SVC appears to have little or no impact on ejection fraction during systole, but reduces wall stress in the ventricles during diastole. Moreover, occlusion of the SVC is expected to be tolerated well by the patient, will not contribute to congestion of the renal or hepatic veins, and will not exacerbate complications often associated with congestive heart failure.

Figure 13:
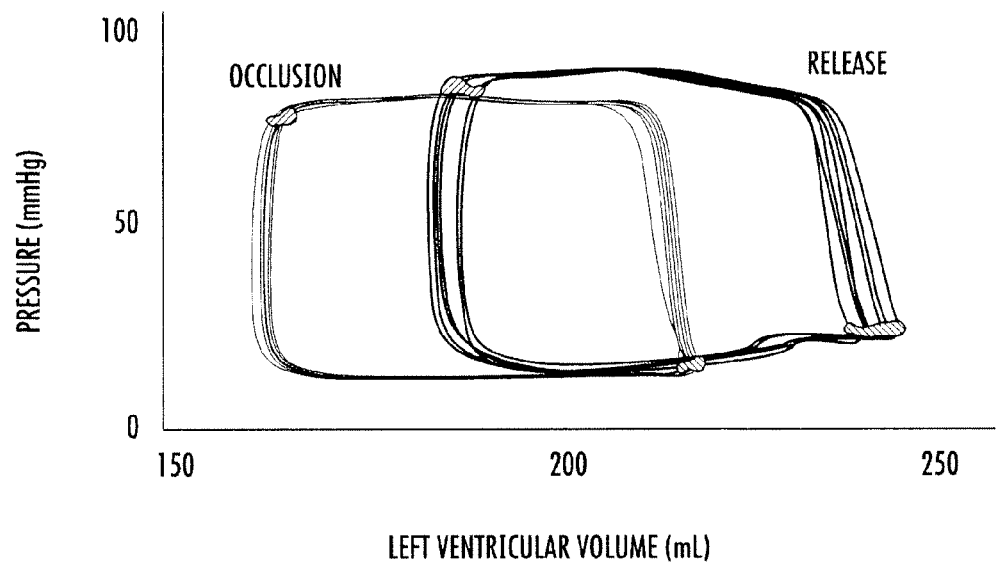
FIGS. 13-14 are graphs showing the changes in pressure as a function of left and right ventricular volume, respectively, during occlusion of the superior vena cava (SVC) and release in a swine subjected to heart failure in accordance with the principles of the present disclosure.
Figure 14:
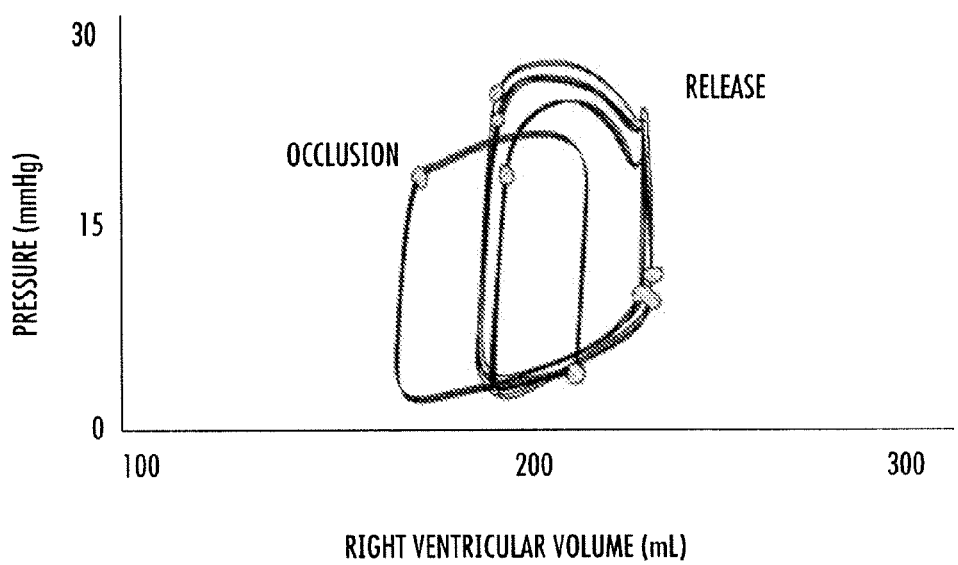

FIGS. 13-14 are graphs showing the changes in pressure as a function of left and right ventricular volume, respectively, during occlusion of the superior vena cava (SVC) and release in a swine treated for heart failure in accordance with the principles of the present disclosure. As shown in the graphs, SVC occlusion led to a significant reduction in left ventricular (LV) volume (240 to 220 mL) and a reduction in LV diastolic pressure (25 to 10 mmHg). SVC occlusion also was associated with reduction in LV systolic pressure (94 to 90 mmHg). SVC occlusion also decreased right ventricular (RV) volume (230 to 210 mL), diastolic pressure (12 to 4 mmHg), and RV systolic pressure (27 to 16 mmHg). Advantageously, SVC occlusion in accordance with the systems and methods described herein reduces biventricular volume and diastolic (filling) pressures without negatively impacting systemic blood pressure (LV systolic pressure). These findings suggest that SVC occlusion has a potentially important beneficial effect on biventricular interaction such that reducing diastolic filling pressures in both ventricles allows for increased ventricular compliance, thereby improving ventricular filling and resulting in increased stroke volume and cardiac output, which is the primary objective when treating a patient with heart failure.

Figure 15:
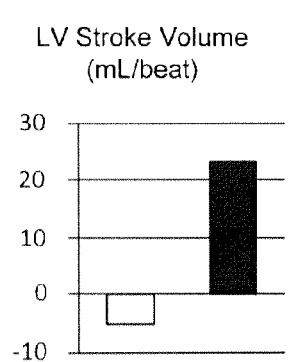
FIGS. 15-22 show test results for swine subjects subjected to heart failure.
Figure 15:
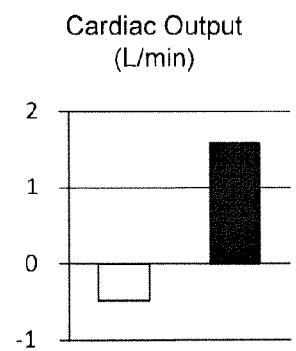
Figure 15:
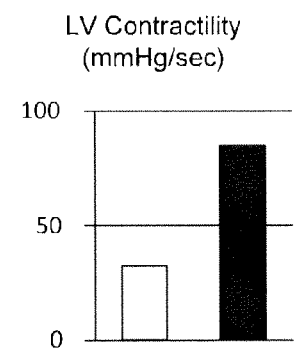
Figure 15:
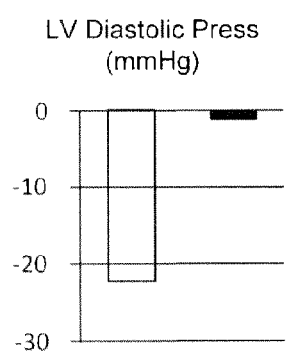
Figure 15:
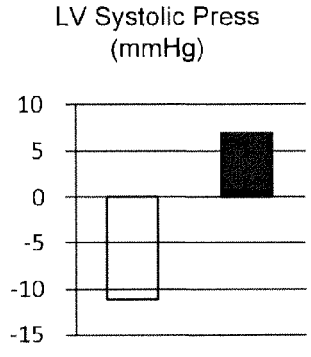
Figure 15:
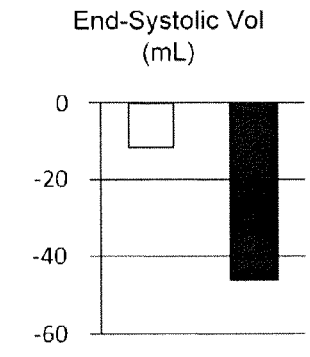

FIG. 15 includes graphs showing that superior vena cava (SVC) occlusion in accordance with the principles of the present disclosure on a swine subject improves cardiac function. The graphs each show the results for partial inferior vena cava (IVC) occlusion (left side of each graph) versus full SVC occlusion (right side of each graph). The graphs show measured left ventricle (LV) stroke volume, cardiac output, LV contractility, LV diastolic pressure, LV systolic pressure, and end-systolic volume.

Figure 16:
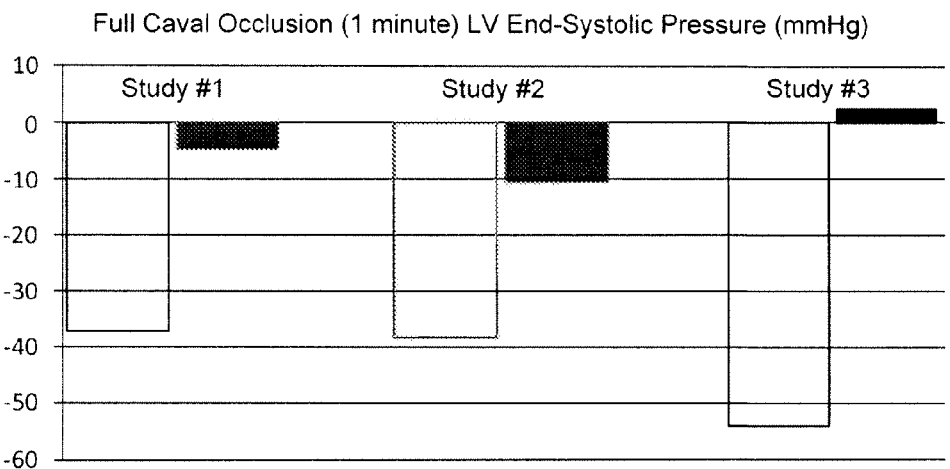

FIG. 16 is graph showing that SVC occlusion in accordance with the principles of the present disclosure on three swine subjects does not harm systolic blood pressure. The graph shows the full caval occlusion (1 minute) LV end systolic pressure (mmHg) for full IVC occlusion (left side of each study) versus full SVC occlusion (right column of each study). Less reduction in LV-end-systolic pressure with SVC occlusion compared to IVC occlusion.

Figure 17:
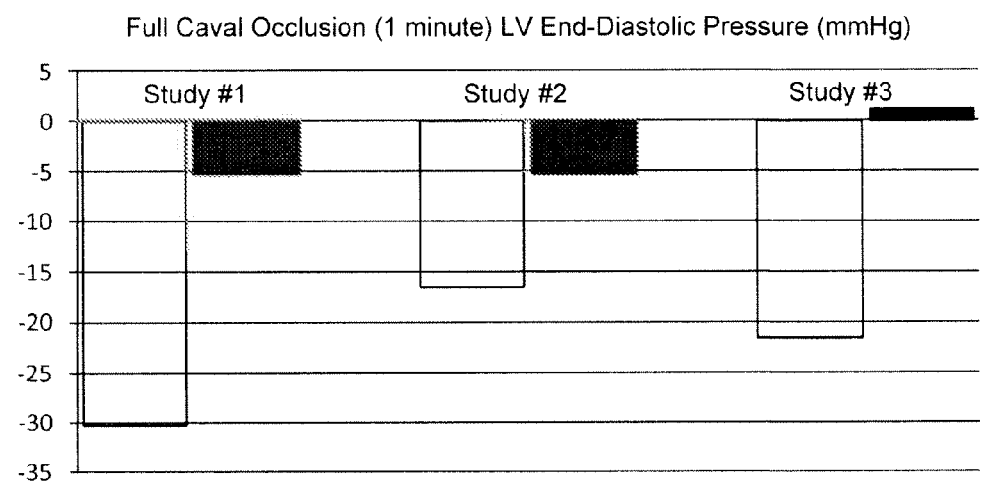

FIG. 17 is graph showing that SVC occlusion in accordance with the principles of the present disclosure on three swine subjects does not harm LV diastolic filling. The graph shows the full caval occlusion (1 minute) LV end diastolic pressure (mmHg) for full IVC occlusion (left side of each study) versus full SVC occlusion (right side of each study). Less reduction in LV-end-diastolic pressure with SVC occlusion compared to IVC occlusion.

Figure 18:
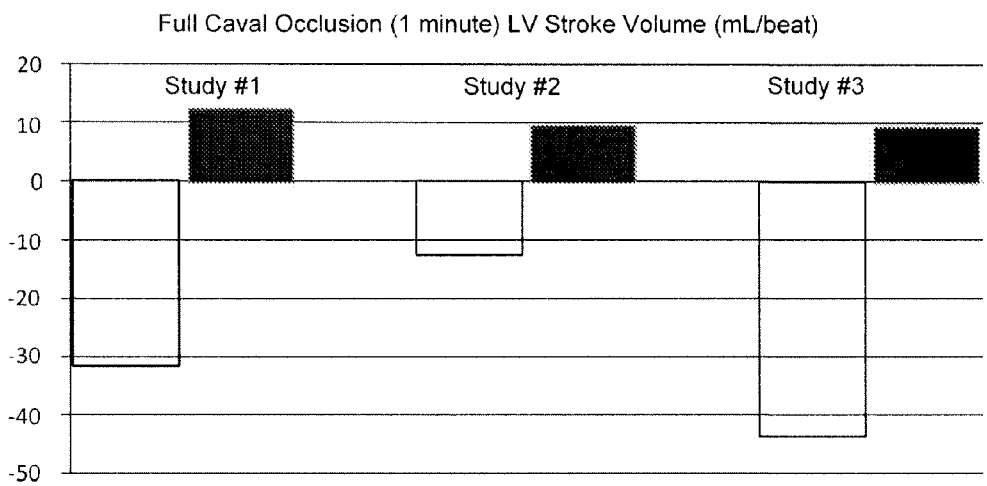

FIG. 18 is graph showing that SVC occlusion in accordance with the principles of the present disclosure on three swine subjects improves LV stroke volume. The graph shows the full caval occlusion (1 minute) LV stroke volume (mL/beat) for full IVC occlusion (left side of each study) versus full SVC occlusion (right side of each study). Increased LV stroke volume with SVC occlusion compared to reduced LV stroke volume IVC occlusion.

Figure 19:
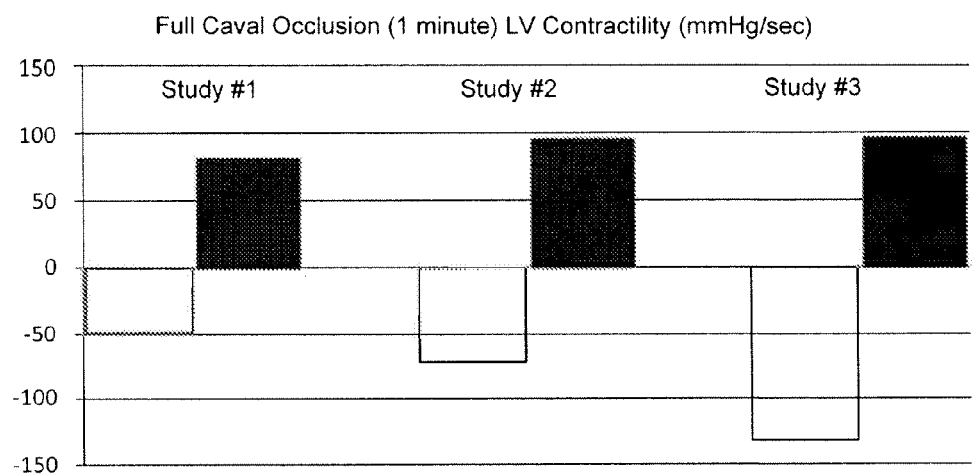

FIG. 19 is graph showing that SVC occlusion in accordance with the principles of the present disclosure on three swine subjects improves LV contractility. The graph shows the full caval occlusion (1 minute) LV contractility (mmHg/sec) for full IVC occlusion (left side of each study) versus full SVC occlusion (right side of each study). Increased LV contractility with SVC occlusion compared to reduced LV contractility with IVC occlusion.

Figure 20:
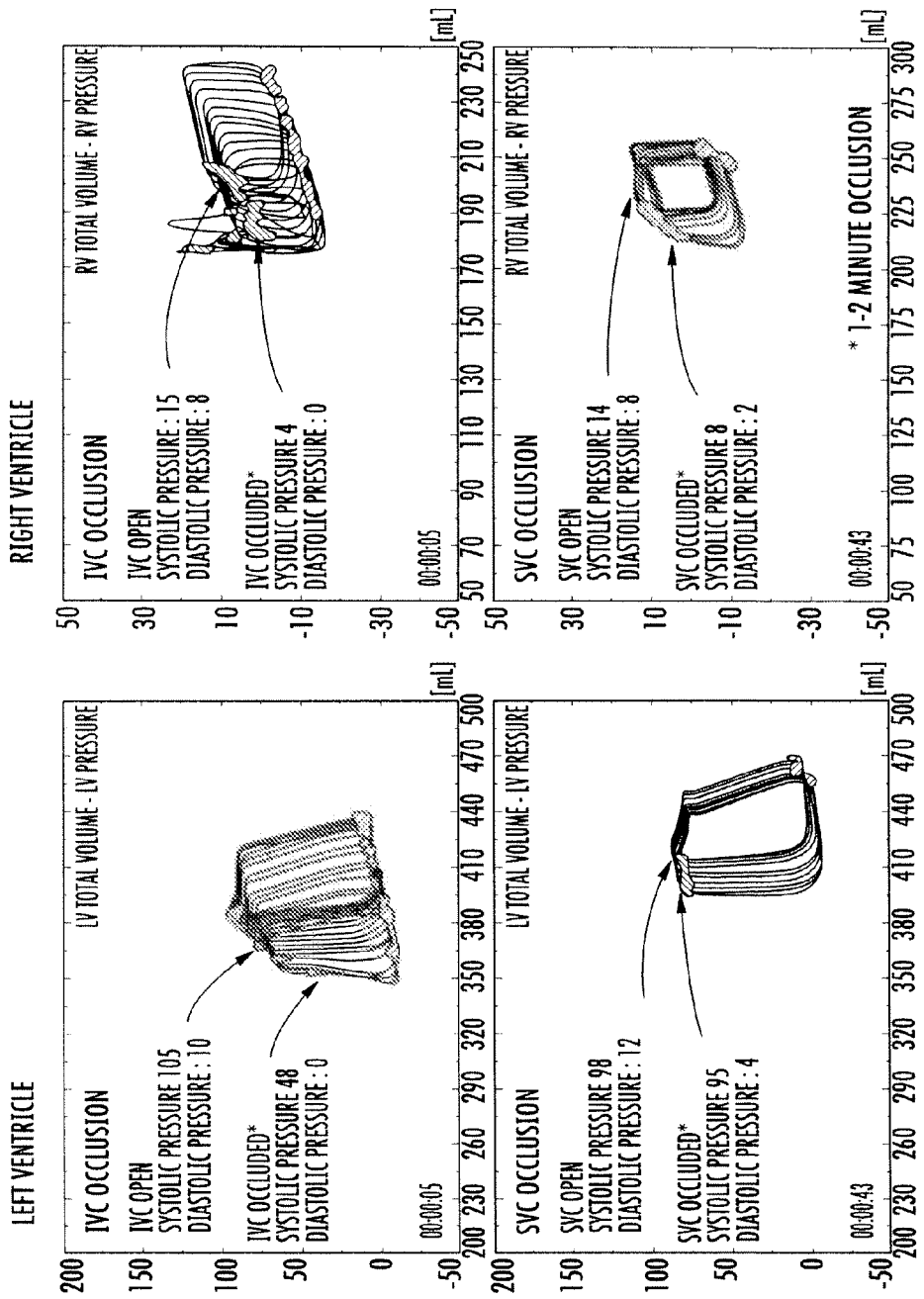

FIG. 20 is four graphs depicting LV total volume and LV pressure for IVC occlusion (upper left), RV total volume and RV pressure for IVC occlusion (upper right), LV total volume and LV pressure for SVC occlusion (lower left), and RV total volume and RV pressure for SVC occlusion (lower right). FIG. 20 illustrates that SVC occlusion provides a significant reduction in LV and RV diastolic pressures without a major reduction in LV systolic pressure as compared to IVC occlusion.

Figure 21:
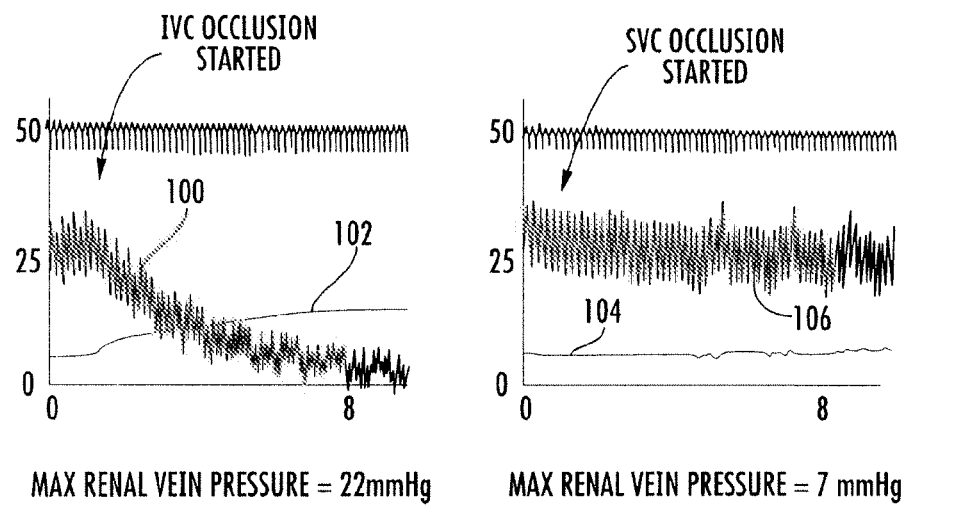

FIG. 21 is two graphs depicting measured pulmonary artery pressure and renal vein pressure in a swine subject for IVC occlusion (left graph) and SVC occlusion (right graph). Line 100 shows the measured pulmonary artery pressure while line 102 shows the measured renal vein pressure for IVC occlusion. Line 104 shows the measured pulmonary artery pressure while line 106 shows the measured renal vein pressure for SVC occlusion. The max renal vein pressure is measured to be 22 mmHg for IVC occlusion whereas the max renal vein pressure is measured to be 7 mmHg for SVC occlusion. FIG. 21 demonstrates that SVC occlusion reduces pulmonary artery pressures without increasing renal vein pressure as compared to IVC occlusion.

Figure 22:
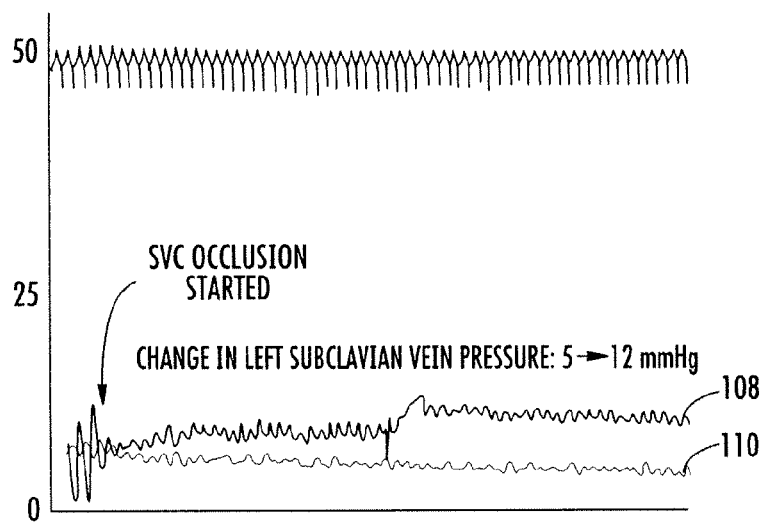

FIG. 22 is a graph depicting measured left subclavian vein pressure and renal vein pressure in a swine subjected to SVC occlusion in accordance with the principles of the present disclosure. Line 108 shows the measured left subclavian vein pressure while line 110 shows the measured renal vein pressure for SVC occlusion. The measured change in left subclavian vein pressure is 5 to 12 mmHg during SVC occlusion. FIG. 22 demonstrates that proximal left subclavian vein pressure increases nominally during SVC occlusion.

Applicants expect that use of the system and methods of the present disclosure for a period of several hours, days, weeks, or months after a patient is admitted to a hospital showing the symptoms of heart failure will result in arresting or reversing further myocardial remodeling and degeneration. In particular, because a system constructed in accordance with the principles of the present disclosure may be designed to be implanted or worn by the patient continuously and in an ambulatory setting, rather than being tethered to a bed, e.g., in an acute-care setting, the patient will see continuous improvement in myocardial function throughout the course of treatment. In addition, by enabling the system to interface with commercially available heart rate monitors and smartphones and/or tablets, the system provides both reduced cost and reduced complexity.

Applicants expect that the systems and methods of the present disclosure may be used alone, as described in the examples, above, or in combination with other devices configured to assist cardiac function, such as an intra-aortic balloon pump ("IABP"), a percutaneous left ventricular assistance device (LVAD) or with a surgical LVAD, thereby allowing for synchronous or asynchronous, (venous and arterial) unloading of cardiac preload and afterload, respectively. By reducing cardiac preload, left ventricular wall tension is reduced, thereby allowing for improved functionality of a left ventricular assist device.

It is to be understood that the foregoing description is intended to illustrate and not to limit the scope of the invention, which is defined by the scope of the appended claims. Other embodiments are within the scope of the following claims.

What is claimed is:

1. A system for treating heart failure in a patient, the apparatus comprising:
a catheter having a proximal end and a distal region, the catheter configured for placement though a subclavian or jugular vein of a patient so that the distal region is disposed in a superior vena cava of the patient;
a flow limiting element disposed on the distal region of the catheter, the flow limiting element configured to be selectively actuated to at least partially occlude the superior vena cava; and
a controller configured to operatively coupled to the catheter to intermittently actuate the flow limiting element to at least partially occlude the superior vena cava over multiple cardiac cycles, the controller including a processor programmed to:
apply a stored value corresponding to a predetermined flow limiting interval during which the flow limiting element is to be actuated;
receive an input corresponding to a physiologic parameter of the patient indicative of fluctuations in the patient's hemodynamic state resulting from the patient's ambulatory activity;
generate an output corresponding to an adjustment of the predetermined flow limiting interval; and
apply the output to revise the predetermined flow limiting interval.

2. The system of claim 1, wherein the proximal end of the catheter is adapted to extend outside the patient and the controller has a size and weight selected to enable the controller to be worn by the patient during ambulatory activity.

3. The system of claim 1, wherein the controller further comprises a drive mechanism configured to be coupled to the flow limiting element of the catheter.

4. The system to claim 1, further comprising a data transfer circuit configured to receive data from a sensor and to provide the input to the processor of the controller.

5. The system of claim 1, wherein catheter comprises one or more sensors.

6. The system of claim 5, wherein the one or more sensors comprise at least a blood pressure sensor and electrodes for detecting a heart rate of the patient.

7. The system of claim 4, wherein the data transfer circuit is configured to wirelessly receive data from a heart rate monitor.

8. The system of claim 4, wherein the data transfer circuit is configured to bi-directionally communicate physiologic data to a computing device of the patient for display to the patient.

9. The system of claim 8, wherein the controller is programmed to send an alert condition to a clinician monitoring the patient via a cellular communications capability of the computing device.

10. The system of claim 3, wherein the flow limiting element is coupled to the drive mechanism via an actuation wire.

11. The system of claim 3, wherein the flow limiting element transitions from a collapsed contracted state to an expanded deployed state when actuated by the drive mechanism.

12. The system of claim 3, wherein the flow limiting element transitions from a collapsed contracted state to an expanded deployed state when actuated by the drive mechanism, and the flow limiting element is configured to transition to the collapsed contracted state if operatively disconnected from the controller.

* * * * *